(12) United States Patent
Graze, Jr.

(10) Patent No.: US 7,406,885 B2
(45) Date of Patent: Aug. 5, 2008

(54) VARIABLE RESPONSE TIME TRANSIENT PARTIAL FLOW SAMPLING SYSTEM AND METHOD

(75) Inventor: Russell R. Graze, Jr., Dunlap, IL (US)

(73) Assignee: Caterpillar Inc., Peoria, IL (US)

( * ) Notice: Subject to any disclaimer, the term of this patent is extended or adjusted under 35 U.S.C. 154(b) by 378 days.

(21) Appl. No.: 11/167,788

(22) Filed: Jun. 27, 2005

(65) Prior Publication Data

US 2006/0288801 A1   Dec. 28, 2006

(51) Int. Cl.
  *G01N 1/00* (2006.01)
(52) U.S. Cl. .................................................. 73/863.01
(58) Field of Classification Search .................. None
  See application file for complete search history.

(56) References Cited

U.S. PATENT DOCUMENTS

| | | | |
|---|---|---|---|
| 5,058,440 A | | 10/1991 | Graze, Jr. |
| 5,535,135 A | * | 7/1996 | Bush et al. ..................... 702/24 |
| 6,062,092 A | * | 5/2000 | Weaver ..................... 73/863.03 |
| 6,615,677 B2 | | 9/2003 | Dickson et al. |
| 2003/0034018 A1 | * | 2/2003 | Baldwin et al. ............. 123/676 |

* cited by examiner

*Primary Examiner*—Robert R Raevis
(74) *Attorney, Agent, or Firm*—Liell & McNeil

(57) ABSTRACT

A partial flow dilution tunnel in a gas sampling system is connected to the exhaust from an internal combustion engine. More accurate gas sampling results are enabled for accounting for a delay from when the engine produces an exhaust change to when that transient arrives at a probe location. Thus, an estimated time delay is determined, and the gas sampling system is operated at least in part based upon that estimated time delay for the exhaust to arrive at the sampling location.

20 Claims, 2 Drawing Sheets

VARIABLE RESPONSE TIME TRANSIENT PARTIAL FLOW SAMPLING SYSTEM AND METHOD

TECHNICAL FIELD

The present disclosure relates generally to the sampling of combustion products for testing, and more particularly to a method of operating a partial flow dilution tunnel in a gas sampling system for testing exhaust from an internal combustion engine.

BACKGROUND

Exhaust gas sampling systems that utilize partial flow dilution tunnels (PFDT) have been used since the early 1990s as an effective alternative to full dilution tunnel systems for development and certification of engines where steady state model testing was permitted. Previously, all off-highway and until recently much of European bound on-highway engine testing and certification was performed with systems utilizing PFDT's, due to the fact that they are more portable, less expensive and often more repeatable than their full dilution counterparts. Regulatory organizations such as ISO, CARB, EPA and EEC all permit the use of PFDT's for steady state test cycle certification. One such system is disclosed in co-owned U.S. Pat. No. 5,058,440, issued on Oct. 22, 1991 to Russell R. Graze, the inventor of the presently claimed subject matter.

More recently, the environmental protection agency has declared its interest in promulgating transient cycle regulations of large off-highway diesel engines in order to better control emissions output from these engines. These regulations are expected to be in effect by 2006. The size of the off-highway diesel engines to be regulated eclipses the mass flow rate capacity of the industries full dilution tunnels that have been in use for the past twenty plus years to quantify on-highway engine emission levels, including particulate matter. Furthermore, the sheer number of off-highway ratings to be developed, in combination with concurrent regulatory pressure placed on-highway engine development times, nearly precludes the use of existing full dilution tunnels for off-highway development, even for small engines.

Therefore, it became desirable to develop a PFDT that could be used to test and certify off-highway diesel engines under transient conditions, and consequently would be also available to be utilized to test on-highway engines under transient conditions as well. One such system is described in co-owned U.S. Pat. No. 6,615,677, issued on Sep. 9, 2003 to Richard R. Dickson and Russell R. Graze. In this system, the mass flow of both air and fuel supplied to the engine are continuously monitored by a controller. When a change is sensed, the controller commands corresponding changes in the gas sampling system in order to accommodate for the inherent change in the exhaust mass flow rate. Although this system has proven effective in quickly responding to transient air and/or fueling supply changes to the engine, there remains room for improvement. For instance, if the controller commands a change to the sampling system too quickly after an air or fuel supply change has occurred, the exhaust may be over or under sampled for a brief duration, resulting in less than satisfactory data. The time lag between changes in the engine exhaust and those changes reaching the gas sampling probe relate to the fact that the probe is typically located downstream in the exhaust stack, and preferably downstream from any exhaust aftertreatment devices. Correctly adjusting for this time lag can be even more difficult if the sampling system is to be made more versatile and useful with a variety of different sized engines.

In the past, in order to perform transient emissions testing, the use of full flow dilution tunnels, or a CVS system, was required. These devices are large, expensive, difficult to maintain and are engine size specific. The co-owned U.S. Pat. No. 6,615,677 responded to this problem by demonstrating a partial flow dilution tunnel that was capable of achieving proportional sampling by rapidly changing dilution air flow to the dilution tunnel described in earlier patent U.S. Pat. No. 5,058,440. These systems operate well in situations where the engine displacement relative to the exhaust system volume does not change appreciably, since the response time of the partial flow sampling system is fixed. However, the current versions do not address applications where the engine size is very small relative to the volume of the exhaust system upstream from the partial flow system sample probe location, or in cases where exhaust after treatment research requires that a significant exhaust system volume be located between the engine and the partial flow system sample probe location. In relatively extreme cases where the ratio of the exhaust volumetric flow rate at standard temperature and pressure to the volume of the exhaust stack between the turbocharger outlet and the sample zone is less than approximately 550:1 for a 300 millisecond response time system, particulate emissions over-sampling can result during accelerations. This is due to the sample mass fraction of the exhaust flow advancing past proportionality. In response to this problem, a modification must be made to the partial flow sampling system to insure that proportional sampling consistently occurs.

The present disclosure is directed to overcoming one or more of the problems set forth above.

SUMMARY OF THE DISCLOSURE

In one aspect, a method of operating a gas sampling system includes a step of estimating a time delay for exhaust to arrive at a sampling area. A proportion of dilution to exhaust sample for the gas sampling system is set at least in part based upon the estimated time delay.

In another aspect, a gas sampling system includes a sampling probe positioned in an exhaust stack section. A controller is operably coupled to control a proportion of dilution to exhaust sample. A computer is operably coupled to the controller and includes a control algorithm operable to estimate a time delay for exhaust to arrive at the sampling probe.

DETAILED DESCRIPTION

Figure 1:
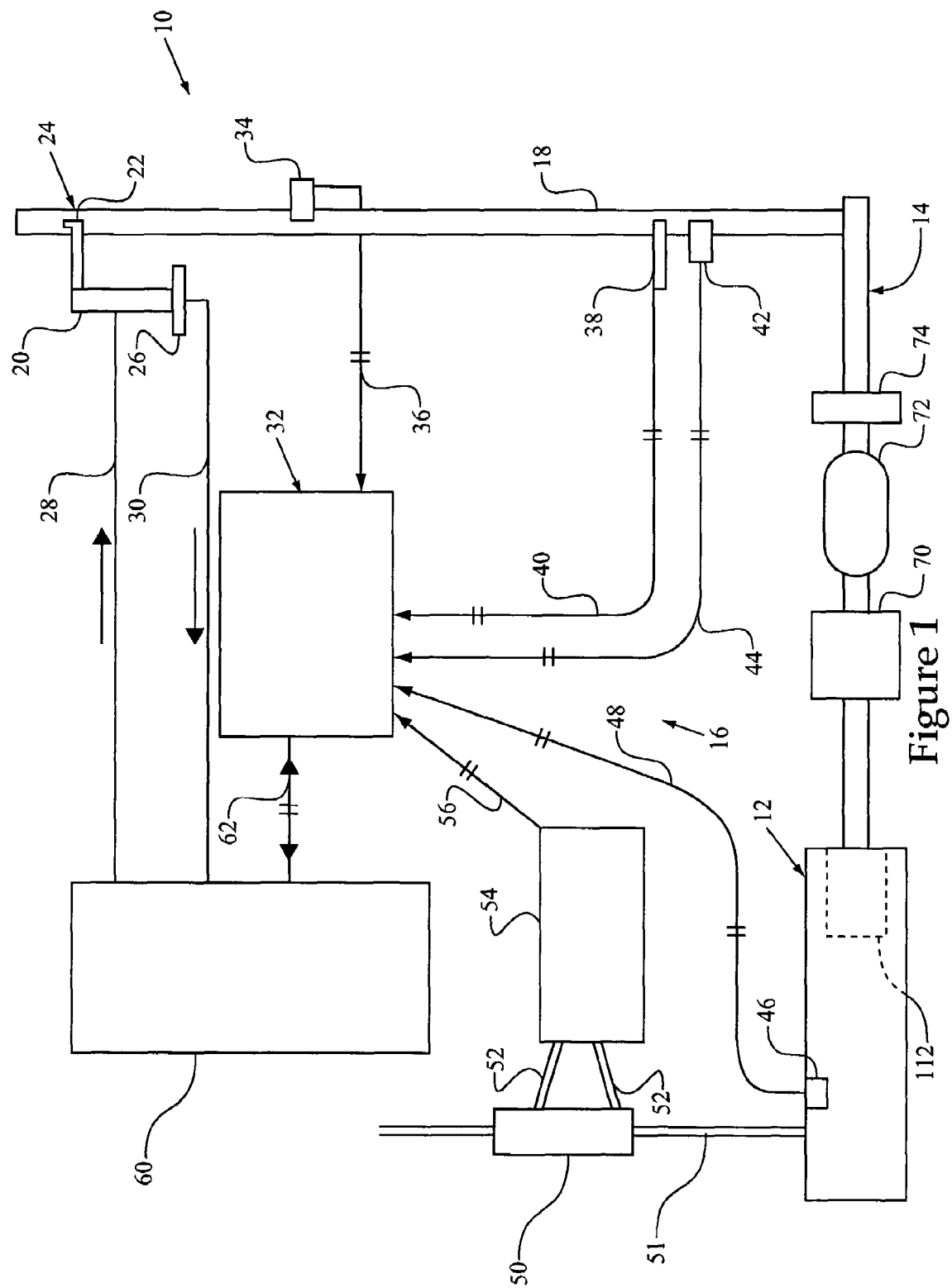
FIG. 1 is a schematic illustration of an engine exhaust test set up that includes a partial flow sampling system according to one aspect of the present disclosure.

Referring to FIG. 1, a test set up 10 includes an engine 12 attached to an exhaust stack 14 and a gas sampling system 16. Set up 10 can accommodate either a relatively large engine 12 or a relatively small engine 112, and provide accurate test results for either. The sampling system 16 includes a computer 32 in communication with a variety of known gas sampling system components 60 and a dilution tunnel 20 that includes a probe 22 positioned at a location 24 in an exhaust stack section 18 of exhaust stack 14. The gas sampling system operates in a conventional manner but is controlled by computer 32 such that a controlled flow rate of dilution air is provided from system components 60 via dilution air supply line 28 to the dilution tunnel assembly 20, in a known manner. A portion of the exhaust gas and any suspended particulate matter are drawn into dilution tunnel 20 via probe 22. At that point, the exhaust and the dilution air are combined, passed through a filter 26, and then sent to gas sampling system components 60 via a sampling mixture line 30 in a conventional manner.

Depending upon the desired level of sophistication, computer 32 controls the dilution air flow rate to accurately test the exhaust from engine 12, 112 during steady state and transient conditions. The problem solved by the present disclosure relates to adjusting operation of the gas sampling system 16 to account for a delay from when the engine 12, 112 produces exhaust until that exhaust arrives at sampling area 24. Those skilled in the art will recognize that this delay is influenced by a variety of factors, which include: the exhaust volumetric flow rate ratio to the exhaust stack volume for a particular engine; time lags in sensing conditions such as intake air supply; time lags in the ability of the gas sampling system 16 to respond to commanded changes; and, possibly even inherent communication rate limitations between the gas sampling system components 60 and/or intake flow rate determining transducer 54 and computer 32. Although many of these time factors are constant and can be determined via known means, such as by testing, the time delay due to exhaust volumetric flow rate and arrival of the exhaust at the sampling point 24 can vary in a less than fully predictable manner across one engine's operating range, and certainly varies from engine to engine, especially when those engines are of substantially different sizes or displacements.

By accurately assessing the volume of exhaust stack 14, one can determine when exhaust from the engine will reach the sampling point 24 by determining the exhaust volumetric flow rate. Depending upon the circumstances, a variety of components may be a portion of, or positioned in, exhaust stack 14. These might include a turbine 70, and/or a variety of exhaust aftertreatment devices such as exhaust catalysts and their associated hardware 72, a particle trap 74, and possibly even an exhaust gas recirculation system (not shown). The present disclosure contemplates operating the gas sampling system 16 in a manner that accounts for the exhaust time delay in a variety of manners, ranging from relatively crude open loop strategies to, and including, self correcting closed loop strategies as described herein.

In one embodiment, a laminar flow element 50 is positioned in the air intake line 51 upstream from engine 12, 112. A pair of pneumatic lines 52 provide pneumatic signals to a differential pressure transducer 54 and provides information to computer 32 via communication line 56 so that the intake air flow rate can be determined by computer 32. Nevertheless, those skilled in the art will appreciate that any suitable means of determining intake air mass flow rate could be substituted in place of the laminar flow element 50 and differential pressure transducer 54 assembly illustrated, without departing from the intended scope of the present disclosure. Thus, any of a variety of known means can be utilized to enable computer 32 to continuously and/or periodically determine the intake air mass flow rate. In addition, the present disclosure contemplates some means for monitoring the fuel supply rate to engine 12, 112. In the illustrated embodiment, this is accomplished by putting computer 32 in communication with the electronic control module 46 for engine 12, such as via a service tool port, which controls the commanded fuel supply to the engine 12, 112. Thus, ECM 46 relates the current fuel supply conditions to computer 32 via communication line 48. However, the present disclosure also contemplates other known means for determining the instantaneous fuel supply rate to engine 12, 112, such as a fuel flow rate meter appropriately positioned in the fuel supply line in a conventional and known manner. Thus, computer 32 can know at any given time the combined mass flow rate of air and fuel to engine 12, 112.

The volumetric exhaust flow rate can be estimated by making certain assumptions and by using known calculating techniques. For instance, if the exhaust gas is assumed to behave as an ideal gas, and if one knows or can estimate the temperature in exhaust stack 14, the ideal gas equation can be utilized to convert the mass flow rate into the engine into an exhaust volumetric flow rate from the engine, assuming a known pressure, such as ambient. In a cruder version of the present disclosure, one could estimate the exhaust gas temperature and determine the exhaust volumetric flow rate from that temperature estimate. In a more enhanced version of the disclosure, temperature of the exhaust is monitored such as by positioning a thermocouple 38 (temperature sensor) at an appropriate location in exhaust stack 14, and communicating a value indicative of exhaust temperature to computer 32 via communication line 40. The accuracy of the calculation to determine exhaust volumetric flow rate can be made even more accurate by also continuously sensing exhaust pressure, such as by positioning an exhaust pressure sensor 42 at an appropriate location in exhaust stack 14, such as in close proximity to thermocouple 38, and communicating a value indicative of exhaust pressure to computer 32 via communication line 44. The pressure and temperature sensors will likely yield better results if placed in close proximity to one another. Thus, assuming that the exhaust were an ideal gas, this would allow for a very accurate determination of the exhaust volumetric flow rate in the vicinity of the temperature and pressure sensors 38 and 42, respectively. This determination can be made further accurate by recognizing that the exhaust actually comprises a less than ideal gas with suspended particles therein. Those skilled in the art will appreciate that the well known ideal gas equation can be adjusted to account for a deviation in the exhaust gas/particle suspension to further refine the determination of exhaust volumetric flow rate. Thus, the present disclosure contemplates a broad range of strategies with any level of desired accuracy that is necessary to produce satisfactory results.

Those skilled in the art will appreciate that estimates of exhaust mass flow rates could also be predetermined for each operating condition of a particular engine, such as via previous lab data. This data could be embedded in the ECM code for the engine, or possibly be determined on board in real time based upon other data originating from the engines ECM. For instance, an estimate of mass flow rate could be determined in real time by reading the commanded fueling rate originating from the ECM along with determining air intake mass flow rate by combining engine speed data with sensed boost pressure in the engines intake manifold. Alternatively, estimates for exhaust mass flow rate could be simply mapped across the engine's operating range and stored in a look up table.

The just described strategies primarily comprise open loop strategies that can be further improved upon by employing a closed loop strategy to periodically or continuously adjust for additional small errors that can be present due to a variety of factors, such as exhaust temperature variations from the sensor location to the sampling location 24, and possibly even variations in the deviation of the exhaust from that of an ideal gas equation across its operating range. In one example closed loop strategy, a transient sensor 34 is positioned in the exhaust stack 14 at an appropriate location with respect to the probe 22. The transient sensor determines when a change in the exhaust has arrived at the transient sensor location, and communicates that timing information to the computer 32. For instance, in the embodiment illustrated, a transient sensor may take the form of a NOx sensor 34 positioned just upstream from probe 22, and communicates a change in NOx content of the exhaust in exhaust stack 14 to computer 32. In the closed loop strategy, computer 32 would continuously predict a time delay for an exhaust change to arrive at the transient sensor 34 location. By comparing the expected arrival time to the actual arrival time of an exhaust transient, the exhaust delay travel time to probe 22 can be further fine tuned to remove any existing errors in the open loop calculations described earlier. As is known in the art, those skilled in the art will appreciate that these various determinations and calculations can be carried out via an appropriate software program reflecting a control algorithm stored on and operated by computer 32 in a known manner.

INDUSTRIAL APPLICABILITY

Figure 2:
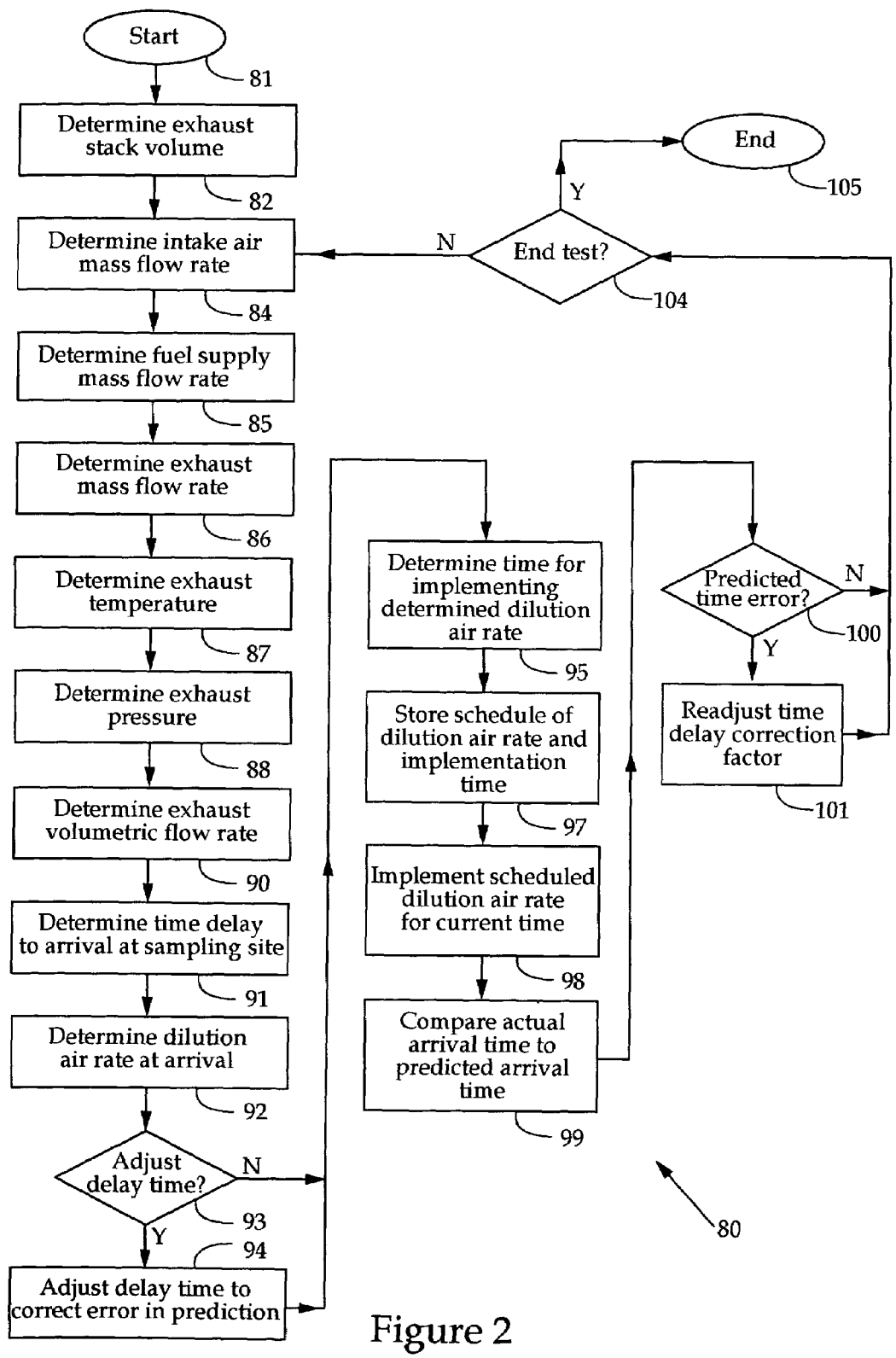
FIG. 2 is a software flow diagram for a control algorithm for use with the partial flow sampling system of FIG. 1.

Referring now to FIG. 2, a software control algorithm operable to run on computer 32 according to one aspect of the disclosure is disclosed. At oval 81, the software is initiated, and the various operating variables might be initialized in a known manner. For instance, an initial time adjustment delay error might be set to zero at this point. At box 82, the exhaust stack volume is determined. In some instances, this value may be a constant for a given test apparatus, or may also have a variable factor due to portions of the exhaust stack associated with a particular engine, including but not limited to exhaust aftertreatment devices. At box 84, the intake air mass flow rate is determined via any of a variety of known means, such as those discussed earlier. At box 85, the fuel supply mass flow rate is determined by any of a variety of means, such as those discussed earlier. Utilizing the intake air mass flow rate and the fuel supply mass flow rate, one can determine the exhaust mass flow rate at box 86 by assuming that the mass flow rate into the engine is about equal to the mass flow rate out of the engine. In box 87, the exhaust temperature is determined, such as via a temperature sensor 38 as shown in FIG. 1. In one version of the present disclosure, no additional sensors are utilized, and the ideal gas equation, or some modification thereof, is utilized with the exhaust mass flow rate and the exhaust temperature to arrive at an estimate of the exhaust volumetric flow rate at box 90. In the illustrated example, this determination is enhanced by determining exhaust pressure at box 88 via an exhaust pressure sensor 42, such as that shown in FIG. 1.

In box 91, the delay time for the exhaust to arrive at the sample site 24 is determined. For instance, one way of arriving at this value would be to divide the exhaust stack volume by the exhaust volumetric flow rate. In box 92, the dilution air rate at the determined arrival time is calculated. Those skilled in the art recognize from teachings known in the art that the dilution air supply rate is often, but not always, inversely proportional to the intake air mass flow rate. Generally there is a base amount of dilution air flow, which may be determined from prior knowledge or other known means. This base amount is a minimum flow required to maintain the peak filter temperature at or below predetermined limits when the engine is at its peak exhaust flow rate. This predetermined limit may relate to statutory regulations in a given jurisdiction. For example, assuming a total flow through the filter 26 is 100 std. liters/minute. The lowest dilution flow value at which one would likely be able to maintain a 52° C. filter face temperature would be about 85 std. liters/minute. That lower number would be the base flow; the dilution flow during actual testing would therefore range from about 85 to nearly 100 std. liters/minute, in one specific example. This would be the range for which the dilution air supply rate would generally be inversely proportional to the engine exhaust flow rate, but in this specific example, the dilution flow rate would never drop below about 85 and never rise above about 100 std. liters/minute. Thus, in the described gas sampling system 16, the dilution air supply rate should be adjusted to correspond to the engine's exhaust rate to generate accurate results in the gas sampling system calculations, which are conveyed to computer 32 via communication line(s) 62, as shown in FIG. 1. In resolver 93, the computer system determines whether there needs to be any adjustment made to the delay time determination. In the first cycles through the system, this should likely return with the answer no. But if the closed loop transient sensor at some later time determines that the delay time estimate is in error, an adjustment factor can be determined and stored and carried forward for application near this location in the control algorithm. If there is a need to adjust the time delay estimate, the control algorithm proceeds to box 94 where an adjustment is made to the delay time calculation to correct for any detected error in the prediction. In box 95, the time for implementing the determined dilution air rate is determined. Box 95 can take into account known features of the system, such as inherent electro-pneumatic mechanical time delays in the gas sampling system components 60 and dilution tunnel assembly 20. Depending upon the particular system, they may determine and store a schedule a predetermined dilution air flow rates and implementation times. In some instances, depending upon the magnitude of the delay from when the exhaust is generated to when it arrives at the sample probe location a relatively long or short schedule may need to be stored in order to accurately operate the gas sampling apparatus 16 to produce accurate results. At box 98, the scheduled dilution air flow rate for a corresponding time is implemented. This box will likely recognize that a dilution air flow rate change must be initiated some finite time before the dilution air flow rate change actually becomes effective due to inherent delays in the system hardware.

At box 99, an aspect of the closed loop strategy is included. At box 99, the actual arrival time at the transient sensor 34 is compared to the predicted arrival time. At resolver 100, if the predicted time is erroneous, preferably beyond some predetermined threshold, a time delay correction factor will be determined at box 101. Thereafter, the flow diagram proceeds to resolver 104 where it is determined whether the test is ended. If so, it proceeds to oval 105 where the control algorithm 80 is ended. Otherwise, the algorithm 80 returns to box 84 to recalculate the intake air mass flow rate. Thereafter, the previously described steps are performed as per control algorithm 80.

By implementing cruder or enhanced versions of the present disclosure, the known gas sampling apparati of the prior art can be enhanced through computer control of the dilution air supply to more accurately reflect time delays from when an engine produces an exhaust gas change to when that change or transient arrives at a sampling probe location. This process can be done in an open loop fashion or in a more accurate closed loop strategy as described. For instance, the most straight forward approach would be to modify the transient partial flow system software as described to impart a delay on the response of the sampling system. The delay may be calculated based upon the volume of the exhaust stack, the exhaust or intake volumetric flow rate imparted to the partial flow system by the engine, intake air fuel flow measurements, for portionality control, and an instantaneous temperature of the exhaust as it approaches the sample zone. In one embodiment, the delay may take the form of a pure time offset; the offset being the difference between the response time of the gas sampling system 16 verse the time of flight of a discrete portion of exhaust in the exhaust stream between the exhaust manifold of the engine or turbocharger outlet and the sample zone location 24.

It should be understood that the above description is intended for illustrative purposes only, and is not intended to limit the scope of the present disclosure in any way. For instance, in one alternative and more simplistic embodiment, the delay may be effected by simply adding volume to the pneumatically active branches of the gas sampling system. However, due to the fact that this will produce more of an averaging effect rather than a clean and accurate offset, this approach is considered less desirable, but nevertheless within the contemplated scope of the present disclosure. The present disclosure could also be applicable to systems that respond to transients by increasing or decreasing the sampling rate rather than by changing the dilution flow rate as in the described embodiment. The disclosure thus contemplates any means for maintaining proportionality in the sample/dilution mixture to accurately produce data representing the actual output from the combustion source, which could be something other than an engine. Thus, those skilled in the art will appreciate that other aspects, objects, and advantages of the disclosure can be obtained from a study of the drawings, the disclosure and the appended claims.

What is claimed is:

1. A method of operating a partial gas sampling system, comprising the steps of:
   estimating a time delay for exhaust to arrive at a sampling area of an exhaust stack;
   setting a proportion of dilution to exhaust sample for the partial gas sampling system at least partially based upon the estimated time delay.

2. The method of claim 1 including changing an air dilution flow rate in response to a change in mass flow of exhaust in the exhaust stack.

3. The method of claim 2 wherein the estimating step includes a step of determining an exhaust stack volume.

4. The method of claim 3 wherein the estimating step includes a step of determining an exhaust temperature; and
   determining an exhaust volumetric flow rate based at least in part on the determined exhaust temperature.

5. The method of claim 4 wherein the estimating step includes a step of determining an exhaust pressure; and
   determining the exhaust volumetric flow rate based at least in part on the determined exhaust pressure.

6. The method of claim 5 including a step of determining an expected time for a portion of exhaust to arrive at a predetermined location in the exhaust stack based at least in part on the estimated time delay; and
   determining an actual arrival time at the predetermined location.

7. The method of claim 6 including a step of comparing the actual arrival time to the expected arrival time; and
   adjusting the estimated time delay based at least in part on the comparison.

8. The method of claim 2 including a step of determining an expected time for a portion of exhaust to arrive at a predetermined location in the exhaust stack based at least in part on the estimated time delay; and
   determining an actual arrival time at the predetermined location.

9. The method of claim 8 including a step of comparing the actual arrival time to the expected arrival time; and
   adjusting the estimated time delay based at least in part on the comparison.

10. The method of claim 1 including the step of detecting an engine transient; and
    changing a dilution air flow rate at a time corresponding to the estimated time delay for the engine transient.

11. The method of claim 1 comprising the step of disconnecting one of a large engine and a small engine from the exhaust stack; and
    connecting an other of the large engine and the small engine to the exhaust stack.

12. A gas sampling system comprising:
    an exhaust stack section;
    a dilution sampling probe positioned in the exhaust stack section;
    a controller operably coupled to control a proportionality of dilution to exhaust sample; and
    a computer in control communication with the controller, and including a control algorithm that includes a time delay estimation algorithm operable to determine a delay time for exhaust to arrive at the dilution sampling probe.

13. The gas sampling system of claim 12 including a temperature sensor operably coupled to sense temperature in the exhaust stack section, and being in communication with the computer.

14. The gas sampling system of claim 13 including a pressure sensor operably coupled to sense a pressure in the exhaust stack section, and being in communication with the computer.

15. The gas sampling system of claim 12 including a transient sensor positioned in the exhaust stack, and being in communication with the computer.

16. The gas sampling system of claim 12 wherein the controller includes means for adjusting a dilution air flow rate.

17. A gas sampling system comprising:
    an exhaust stack section;
    a sampling probe positioned in the exhaust stack section;
    a controller operably coupled to control a proportionality of dilution to exhaust sample;
    a computer in control communication with the controller, and including a control algorithm that includes a time delay estimation algorithm operable to determine a delay time for exhaust to arrive at the sampling probe; and
    the control algorithm includes means for determining an exhaust volumetric flow rate.

18. A gas sampling system comprising:
    an exhaust stack section;
    a sampling probe positioned in the exhaust stack section;
    a controller operably coupled to control a proportionality of dilution to exhaust sample;
    a computer in control communication with the controller, and including a control algorithm that includes a time delay estimation algorithm operable to determine a delay time for exhaust to arrive at the sampling probe;
    a transient sensor positioned in the exhaust stack, and being in communication with the computer; and the control algorithm includes a time delay estimation adjustment algorithm operable to compare an estimated time delay to a sensed time delay for an exhaust transient to arrive at the transient sensor.

19. The gas sampling system of claim 18 wherein the transient sensor includes a NOx sensor.

20. The gas sampling system of claim 19 including a temperature sensor operably coupled to sense temperature in the exhaust stack section, and being in communication with the computer.

* * * * *